United States Patent
Zhang et al.

(10) Patent No.: US 11,098,282 B1
(45) Date of Patent: Aug. 24, 2021

(54) SERUM-FREE CULTURE MEDIUM FOR IN VITRO MATURATION OF BOVINE OOCYTES AND A METHOD FOR CULTURE OF OOCYTES

(71) Applicant: NORTHWEST A&F UNIVERSITY, Xianyang (CN)

(72) Inventors: Jingcheng Zhang, Xianyang (CN); Yuemeng Huang, Xianyang (CN); Min Zhang, Xianyang (CN); Debao Wang, Xianyang (CN); Yong Wang, Xianyang (CN); Yong Zhang, Xianyang (CN)

(73) Assignee: NORTHWEST A&F UNIVERSITY, Xianyang (CN)

( * ) Notice: Subject to any disclaimer, the term of this patent is extended or adjusted under 35 U.S.C. 154(b) by 0 days.

(21) Appl. No.: 17/013,798

(22) Filed: Sep. 7, 2020

Related U.S. Application Data

(63) Continuation of application No. PCT/CN2020/100828, filed on Jul. 8, 2020.

(30) Foreign Application Priority Data

Jun. 22, 2020 (CN) .......................... 202010575024.5

(51) Int. Cl.
*C12N 5/075* (2010.01)
*C12N 5/00* (2006.01)

(52) U.S. Cl.
CPC .......... *C12N 5/0609* (2013.01); *C12N 5/0037* (2013.01); *C12N 2500/90* (2013.01); *C12N 2501/11* (2013.01); *C12N 2501/115* (2013.01)

(58) Field of Classification Search
CPC ............... C12N 5/0609; C12N 5/0037; C12N 2500/90; C12N 2501/11; C12N 2501/115
See application file for complete search history.

(56) References Cited

FOREIGN PATENT DOCUMENTS

CN 108103011 A * 6/2018

* cited by examiner

*Primary Examiner* — Thaian N. Ton

(57) ABSTRACT

A serum-free culture medium for in vitro maturation of bovine oocytes includes a Hepes-free M199 basal medium, fatty acid-free BSA, human menopausal gonadotrophin (HMG), 17β-estradiol, epidermal growth factor (EGF), L-cysteine, bFGF, Glutamax (100×), folic acid, cholic acid and CXCL12. A method of culturing bovine oocytes using such serum-free culture medium is provided.

7 Claims, No Drawings

SERUM-FREE CULTURE MEDIUM FOR IN VITRO MATURATION OF BOVINE OOCYTES AND A METHOD FOR CULTURE OF OOCYTES

TECHNICAL FIELD

This disclosure relates to cell culture, and more particularly to a serum-free culture medium for the in vitro maturation of bovine oocytes and a method for the culture of oocytes.

BACKGROUND

In vitro maturation of oocytes plays a fundamental and crucial role in the embryo engineering such as in vitro fertilization, somatic cell nuclear transfer (SCNT), in vitro production of animal embryos and transgenic cloning. However, the in vitro maturation of oocytes is not only affected by various factors such as ovarian cycle, animal species, follicle size, hormones and serum, but also closely associated with the employed procedures and methods and the composition of the culture medium. Particularly, the serum will lead to the occurrence of fetal macrosomia in the in vitro embryonic production. Though great progress has been made in the in vitro maturation techniques of oocytes recently, there is still no report on the research about serum-free culture system.

Therefore, there is an urgent need for those skilled in the art to provide a serum-free culture medium for the in vitro maturation of bovine oocytes and a culture method for oocytes.

SUMMARY

In view of this, an object of this disclosure is to provide a serum-free culture medium for the in vitro maturation of bovine oocytes and a method for the culture of oocytes, in order to improve the in vitro maturation rate of bovine oocytes and reduce the occurrence of fetal macrosomia caused by serum.

Technical solutions of this application are described as follows.

In a first aspect, this application provides a serum-free culture medium for in vitro maturation of bovine oocytes, comprising: a Hepes-free M199 basal medium, 2-8 mg/mL of fatty acid-free BSA, 0.05-0.1 IU/mL of human menopausal gonadotrophin (HMG), 0.1-2 µg/mL of 17β-estradiol, 1-100 ng/mL of epidermal growth factor (EGF), 0.1-1 mM of L-cysteine, 1-100 ng/mL of bFGF, 0.5-2 µL/mL of Glutamax (100×), 1-100 µM of folic acid, 1-10 µg/mL of cholic acid and 1-100 ng/mL of CXCL12.

In an embodiment, the serum-free culture medium for in vitro maturation of bovine oocytes comprises: a Hepes-free M199 basal medium, 6 mg/mL of fatty acid-free BSA, 0.075 IU/mL of HMG, 1 µg/mL of 17β-estradiol, 60 ng/mL of EGF, 0.57 mM of L-cysteine, 40 ng/mL of bFGF, 1.6 µL/mL of Glutamax (100×), 50 µM of folic acid, 2 µg/mL of cholic acid and 50 ng/mL of CXCL12.

In a second aspect, this application provides a culture method for in vitro maturation of bovine oocytes using the above serum-free culture medium, comprising:

pre-heating the serum-free culture medium; and culturing the bovine oocytes in the pre-heated serum-free culture medium at 38.5° C. and 5% $CO_2$ under saturated humidity for 18-22 h to obtain mature bovine oocytes.

In an embodiment, the bovine oocytes are germinal vesicle (GV) oocytes.

In an embodiment, the serum-free culture medium is pre-heated for 1-3 h.

In an embodiment, the pre-heating is performed at 38.5° C. and 5% $CO_2$ under saturated humidity.

In an embodiment, an initial density in the culturing is 40-50 bovine oocytes per 500 µL of the serum-free culture medium.

Compared to the prior art, the present invention has the following beneficial effects.

The serum-free culture medium for the in vitro maturation of bovine oocytes and a culture method for oocytes provided by the present invention can improve the in vitro maturation rate of bovine oocytes, and at the same time, effectively promote the early development of in vitro fertilized embryos and somatic nuclear transferred embryos.

DETAILED DESCRIPTION OF EMBODIMENTS

The technical solutions of the present invention will be clearly and fully described below with reference to the embodiments. It should be understood that these embodiments are merely illustrative of the invention without limiting. Any other embodiments obtained by those skilled in the art based on the content disclosed herein without sparing any creative effort should fall within the scope of the present invention.

Hepes-free M199 basal medium is purchased from Thermo Fisher Scientific Inc. Defined FBS is purchased from GIBCO Company. Fibroblast growth factor (FGF), epidermal growth factor (EGF) and CXCL12 are purchased from R&D Systems Co., Ltd. Other unspecified reagents are all purchased from Sigma-Aldrich Inc.

Preparation of Oocyte Collection Solution (PBS)

26.168 mg of $CaCl_2.2H_2O$, 37.218 mg of $MgSO4.7H_2O$, 0.0203 g of KCl, 0.0200 g of $KH_2PO_4$, 0.0036 g of sodium pyruvate, 0.805 g of NaCl, 0.1153 g of $Na_2HPO_4$, 0.1 g of D-glucose, 6 mg of heparin sodium and 3 mL of FBS are mixed, diluted with deionized water to 100 mL and adjusted to pH 7.0-7.2 with 1 mM NaOH to prepare the oocyte collection solution.

Preparation of a synthetic oviduct fluid (SOF)

0.6294 g of NaCl, 0.0534 g of KCl, 0.162 g of $KH_2PO_4$, 0.0172 g of $CaCl_2.2H_2O$, 0.00996 g of $MgCl_2.6H_2O$, 0.2106 g of $NaHCO_3$, 0.0033 g of sodium pyruvate and 77.55 µL of 60% (w/w) sodium lactate are added to 98 mL of water, and then the system is adjusted to pH 7.2-7.4 with 1 mM NaOH and diluted to 100 mL with eionized water to produce the SOF.

Preparation of SOFaa Solution

The SOF is used as basic medium and added with 1% by volume of essential amino acids, 1% by volume of non-essential amino acids, 6 mg/mL of fatty acid-free bovine serum albumin (BSA), 12 µg/mL of gentamicin and 12 µg/mL of cephalosporin to prepare the SOFaa solution.

Preparation of mSOFaa Solution

The SOFaa solution is used as basic medium and added with 1% by volume of ITS-G, 55 µM of β-mercaptoethanol, 2.5 mM of hypotaurine, 0.4 µg/mL of 1-oleoyl-SN-glycero-3-phosphate (sodium salt), 0.1 mM of salidroside, 10 ng/mL of progesterone, 100 µM of vitamin E, 1 mM of L-carnitine, 40 ng/mL of FGF, 10 ng/mL of corticosterone, 20 ng/mL of EGF, 25 ng/mL of insulin-like growth factor (IGF), 20 ng/mL of LIF and 2 mg/mL of hyaluronic acid during the pre-heating to prepare the mSOFaa solution.

Preparation of Electrofusion Medium

The electrofusion medium contains 0.3 mol/L of mannitol, 0.05 mol/L of calcium chloride, 0.1 mol/L of magnesium sulfate, 0.27 mol/L of histidine and 1 mg/mL of BSA.

Preparation of Fertilization Medium

An inositol-free SOF is used as basic medium and added with 8 mg/mL of fatty acid-free BSA, 12 μg/mL of gentamicin, 12 μg/mL of cephalosporin, 63 μg/mL of L-arginine, 6 μg/mL of L-aspartic acid, 50 μM of L-carnitine, 2 mM of adrenaline, 20 mM of penicillamine, 10 mM of hypotaurine and 10 μg/mL of heparin to prepare the fertilization medium.

Example 1

Provided herein was a serum-free culture medium for the in vitro maturation of bovine oocytes, which contained a Hepes-free M199 basal medium, 6 mg/mL of fatty acid-free BSA, 0.075 IU/mL of HMG, 1 μg/mL of 17β-estradiol, 60 ng/mL of EGF, 0.57 mM of L-cysteine, 40 ng/mL of bFGF, 1.6 μL/mL of Glutamax (100×), 50 μM of folic acid, 2 μg/mL of cholic acid and 50 ng/mL of CXCL12.

Comparative Example 1

Provided herein was a serum-containing culture medium for the in vitro maturation of bovine oocytes, which contained a Hepes-free M199 basal medium, 10% by volume of FBS, 0.075 IU/mL of HMG, 1 μg/mL of 17β-estradiol, 10 ng/mL of EGF, 1% by volume of insulin-transferrin-selenium (ITSG), 10 ng/mL of bFGF and 50 ng/mL of CXCL12.

Comparative Example 2

Provided herein was a serum-free culture medium for the in vitro maturation of bovine oocytes, which contained a Hepes-free M199 basal medium, 6 mg/mL of fatty acid-free BSA, 0.075 IU/mL of HMG, 1 μg/mL of 17β-estradiol, 10 ng/mL of EGF, 1% by volume of ITSG, 10 ng/mL of bFGF and 50 ng/mL of CXCL12.

Example 2

In Vitro Maturation of Bovine Oocytes

Bovine ovaries were collected from a designated slaughterhouse in Xi'an (Shaanxi Province), stored in normal saline containing 100 IU/mL of penicillin and 100 μg/mL of streptomycin at 20-25° C. in a thermos and transported to the laboratory within 5 h. Then the connective tissues, fat and fallopian tubes attached on the surface of the ovaries were removed by a sterilized scissor, and the remaining ovarian tissues were washed three times with sterile normal saline. Oocytes in the 2-8 mm follicles on the ovarian surface were harvested with a 10 mL syringe equipped with a 21G needle, placed in a 6 cm culture dish and observed under a stereomicroscope to collect cumulus-oocyte complexes (COCs). After washed three times with PBS, those COCs in which the oocytes had normal morphology were selected for the in vitro maturation.

Experimental Group

The selected COCs were washed twice with the serum-free culture medium provided in Example 1 and then transferred to a 3 cm culture dish containing 3 mL of the serum-free culture medium provided in Example 1, which was equilibrated in an incubator for 1 h in advance. The COCs were cultured at 38.5° C. and 5% $CO_2$ under saturated humidity for 18-22 h, and the mature COCs were washed three times with PBS, digested in PBS with 0.1% hyaluronidase and without $Ca^{2+}$ and $Mg^{2+}$ for 1-2 min and pipetted repeatedly with a 1000 mL pipette to remove the diffused cumulus cells outside the oocytes. After that, the remaining oocytes were washed three times with PBS and observed under the stereomicroscope, where those oocytes with a polar body were collected with a foreign body needle for use.

Control Group 1

The selected COCs were washed twice with the serum-containing culture medium provided in Comparative Example 1 and then transferred to a 3 cm culture dish containing 3 mL of the serum-containing culture medium provided in Comparative Example 1, which was equilibrated in an incubator for 1 h in advance. The COCs were cultured at 38.5° C. and 5% $CO_2$ under saturated humidity for 18-22 h, and the mature COCs were washed three times with PBS, digested in PBS with 0.1% hyaluronidase and without $Ca^{2+}$ and $Mg^{2+}$ for 1-2 min and pipetted repeatedly with a 1000 mL pipette to remove the diffused cumulus cells outside the oocytes. After that, the remaining oocytes were washed three times with PBS and observed under the stereomicroscope, where those oocytes with a polar body were collected with a foreign body needle for use.

Control Group 2

The selected COCs were washed twice with the serum-free culture medium provided in Comparative Example 2 and then transferred to a 3 cm culture dish containing 3 mL of the serum-free culture medium provided in Comparative Example 2, which was equilibrated in an incubator for 1 h in advance. The COCs were cultured at 38.5° C. and 5% $CO_2$ under saturated humidity for 18-22 h, and the mature COCs were washed three times with PBS, digested in PBS with 0.1% hyaluronidase and without $Ca^{2+}$ and $Mg^{2+}$ for 1-2 min and pipetted repeatedly with a 1000 mL pipette to remove the diffused cumulus cells outside the oocytes. After that, the remaining oocytes were washed three times with PBS and observed under the stereomicroscope, where those oocytes with a polar body were collected with a foreign body needle for use.

The in vitro maturation condition of the oocytes in each group was observed and recorded, and the results were shown in Table 1.

TABLE 1

In vitro maturity of oocytes in different groups

| Groups | Total number of oocytes | Number of mature oocytes (maturation rate %: number of mature oocytes/total number of oocytes) |
|---|---|---|
| Experimental group | 345 | 254 (73.62%)[b] |
| Control group 1 | 366 | 232 (63.39%)[a] |
| Control group 2 | 315 | 186 (59.05%)[a] |

Notes: different superscripts indicated significant difference; and the significance analysis was performed using chi-square test.

It can be seen from Table 1 that compared to the serum-containing culture medium provided in Comparative Example 1 and the serum-free culture medium provided in Comparative Example 2, the serum-free culture medium provided in Example 1 can significantly improve the in vitro maturation rate of bovine oocytes.

Example 3

Preparation of Bovine Somatic Cell Cloned Embryos (1) Culture of Bovine Fetal Fibroblasts A tube of bovine fetal fibroblasts (collected from a cattle farm owned by Yangling Keyuan Clone Co., Ltd) from $2^{nd}$ to $5^{th}$ generation of Holstein cows was transferred from liquid nitrogen, thawed at 39° C. and suspended with 0.8 mL of DMEM/F12 medium. The cell suspension was centrifuged, and the supernatant was discarded. Then the cells were resuspended with the cell culture medium, and 3 mL of the cell resuspension was inoculated to a culture dish with a diameter of 6 cm, which was subsequently cultured at 38.5° C. in a $CO_2$ incubator.

When the bovine fetal fibroblasts grew to a confluence of 80%, the culture medium was removed, and the cells were washed with a $Ca^{2+}$ and $Mg^{2+}$-free PBS, digested with a mixed solution of trypsin and EDTA and observed under an inverted microscope. When most of the cells contracted and rounded, and the intercellular space increased, the digestion was terminated with a DMEM/F12 medium containing 10% fetal bovine serum, and the cell suspension was pipetted with a pipette and centrifuged. The cells were suspended, inoculated into a 24-well plate at a ratio of 1:3 and cultured in the $CO_2$ incubator. The medium was replaced with a DMEM/F12 medium containing 0.5% fetal bovine serum two days before the preparation of somatic cell cloned embryos.

(2) Maturation of Oocytes

The in vitro maturation of oocytes was the same as that in Example 2.

(3) Construction of Bovine Somatic Cell Cloned Embryos

Enucleation

Before the enucleation, the oocytes in the Experimental group and Control groups 1 and 2 were respectively incubated in a M199 medium containing 7.5 μg/mL of cytochalasin B, 4 mg/mL of fatty acid-free BSA and Hepes for 15 min. Under the micromanipulator, an enucleating tube with an inner diameter of 20 μm was employed to extract the first polar body and some of the surrounding protruding ooplasm.

Injection and Electrical Fusion

Bovine fetal fibroblasts with a size of 15-20 μm were selected and transferred into the zona pellucida of the enucleated oocytes in the Experimental group and Control groups 1 and 2, respectively. Then the reconstructed embryos were subjected to electrical fusion using a microelectrode. The reconstructed embryos were pre-equilibrated in the electrofusion solution for 3 min before the fusion, and the electrofusion was performed under a 150× micromanipulator. A top diameter of the two "Z"-shaped microelectrodes for fusion was 15 μm, and a rear end of each microelectrode was connected to the micromanipulator to render the membrane contact surface of the donor and acceptor of the reconstructed embryo perpendicular to the connecting line between the two electrodes. The fusion parameters were set as follows: voltage: 32V; pulse duration: 20 μs; pulse interval: 10 ms. The reconstructed embryos were observed under the microscope half an hour after the fusion, and the successfully-fused embryos were respectively cultured in the culture mediums provided in Example 1 and Comparative Examples 1-2 for 3 h.

(4) Activation of Bovine Somatic Cell Cloned Embryos 3 hours after electrofusion, the bovine somatic cell cloned embryos in Experimental group and Control groups 1 and 2 were activated with ionomycin in combination with 6-DMAP. Specifically, the cloned embryos were cultured in a SOFaa medium containing 2-5 μmon of ionomycin at room temperature for 4 min, and then cultured in a SOFaa medium containing 1-2 mmol/L of 6-DMAP at 38.5° C. and 5% $CO_2$ under saturated humidity for 4 h.

(5) In Vitro Culture of Bovine Somatic Cell Cloned Embryos

500 μL of the mSOFaa solution was added to each well of a 4-well plate and then covered with 500 μL of paraffin oil, where the paraffin oil was pre-equilibrated in a $CO_2$ incubator for at least 2 h. The activated bovine somatic cell cloned embryos in the Experimental group and Control groups 1 and 2 were respectively transferred to the above 4-well plate with 35-40 embryos per well, and cultured at 38.5° C., 5% $CO_2$ and 7% $O_2$ under saturated humidity. The development status was recorded and shown in Table 2.

TABLE 2

Development status of cloned embryos

| Group | Total number of oocytes | Number of cleavage embryos (cleavage rate %: number of cleavage embryos/ total number of oocytes) | Number of blastocysts at the $7^{th}$ day (rate %: number of blastocysts/ number of cleavage embryos) | Number of blastocysts of the grades A and B at the $7^{th}$ day (rate %: number of blastocysts of the grades A and B/ number of blastocysts) |
|---|---|---|---|---|
| Experimental group | 136 | 106 (77.94%) | 39 (36.79%)[b] | 22 (56.41%)[b] |
| Control group 1 | 145 | 109 (75.17%) | 35 (32.11%)[b] | 15 (42.86%)[a] |
| Control group 2 | 69 | 48 (69.57%) | 11 (22.92%)[a] | 4 (36.36)[c] |

Notes: different superscripts indicated significant difference; the significance analysis was performed by chi-square test; blastocysts of grades A and B were transplantable; blastocysts of grade C were not recommended for transplantation; the grading of blastocysts was determined according to the blastocyst quality scoring criteria published by International Embryo Transfer Association.

It can be concluded from Table 2 that compared to the in vitro serum-containing culture system in Control group 1 and the in vitro serum-free culture system in Control group 2, the in vitro serum-free culture system of the present invention can significantly improve the ratio of the transplantable blastocysts after the nuclear transfer.

Example 4

Preparation of In Vitro Fertilized Bovine Embryos (1) Maturation of Oocytes

The maturation of oocytes was performed according to the process mentioned in Example 2.

(2) Thawing, Purification and Fertilization of Sperms

Cryopreserved sperms (Inner Mongolia SK•Xing Co., Ltd) were transferred from liquid nitrogen and thawed in a 38.5° C. water bath. A percoll gradient was prepared in a centrifugation tube with 2 mL of 90% Percoll at the bottom and 2 mL of 45% Percoll layered thereon. Then the thawed sperms were carefully placed on the 45% Percoll layer and centrifuged at 1,500 rpm for 20 min. About 200 μL of the semen at the bottom was carefully pipetted and added to the fertilization system containing the oocytes respectively of the Experimental group, Control group 1 and Control group 2. The fertilization system was cultured in an incubator for 8-12 h to perform the sperm-egg fusion.

(3) Culture of Fertilized Embryos

After the fertilization was completed, the remaining cumulus cells and sperms around the egg were removed with a mouth pipette or a pipette. A hyaluronidase solution can be introduced to completely eliminate the remaining cumulus cells and sperms. The fertilized embryos were then cultured in the mSOFaa medium which was covered with 500 μL of paraffin oil on the surface and pre-equilibrated in a $CO_2$ incubator for at least 2 h, and the development status was recorded and shown in Table 3.

The bovine oocytes were placed in the pre-heated serum-free culture medium provided herein and then cultured at 5% $CO_2$ for 18-22 h to obtain mature oocytes. It had been demonstrated by experiments that the culture medium for the in vitro maturation and the in vitro maturation method provided herein can significantly improve the in vitro maturation rate of bovine oocytes.

The description of the above embodiments is intended to enable those skilled in the art to implement and use the invention, and is not intended to limit the invention. Any modifications, changes and replacements made by those skilled in the art without departing from the spirit of the invention should fall within the scope of the invention.

What is claimed is:

1. A serum-free culture medium for in vitro maturation of bovine oocytes, comprising:
   a Hepes-free M199 basal medium,
   2-8 mg/mL of fatty acid-free bovine serum albumin (BSA),
   0.05-0.1 IU/mL of human menopausal gonadotrophin (HMG),
   0.1-2 μg/mL of 17 β-estradiol,
   1-100 ng/mL of epidermal growth factor (EGF),
   0.1-1 mM of L-cysteine,
   1-100 ng/mL of bFGF,
   0.5-2 μL/mL of L-alanyl-L-glutamine dipeptide,
   1-100 μM of folic acid,
   1-10 μg/mL of cholic acid and
   1-100 ng/mL of CXCL 12.

2. The serum-free culture medium of claim 1, comprising:
   6 mg/mL of fatty acid-free BSA,
   0.075 IU/mL of HMG,
   1 μg/mL of 17β-estradiol,
   60 ng/mL of EGF,

TABLE 3

Development of *in vitro* fertilized embryos

| Group | Total number of cumulus-oocyte complexes | Number of cleavage embryos (rate %: number of cleavage embryos/ total number of cumulus-oocyte complexes) | Number of blastocysts of the 7$^{th}$ day (rate %: number of blastocysts/ number of cleavage embryos) | Number of blastocysts at the grades A and B at the 7$^{th}$ day (rate %: number of blastocysts of the grades A and B/ number of blastocysts) |
|---|---|---|---|---|
| Experimental group | 177 | 102 (57.63%) | 26 (25.49%)$^b$ | 19 (73.08%)$^b$ |
| Control group 1 | 185 | 97 (52.43%) | 23 (23.71%)$^b$ | 15 (65.22%)$^a$ |
| Control group 2 | 164 | 80 (48.78%) | 12 (15.00%)$^a$ | 3 (25.00%)$^c$ |

Notes: different superscripts indicated significant difference; the significance analysis was performed by chi-square test; blastocysts of grades A and B were transplantable; blastocysts of grade C were not recommended for transplantation; the grading of blastocysts was determined according to the blastocyst quality scoring criteria published by International Embryo Transfer Association.

It can be seen from Table 3 that compared to the in vitro serum-containing culture system in Control group 1 and the in vitro serum-free culture system in Control group 2, the in vitro serum-free culture system of the invention can significantly improve the ratio of the transplantable blastocysts after the fertilization.

The serum-free culture medium provided herein for the in vitro maturation of bovine oocytes contained a basal medium and some supplementary components such as BSA, EGF, L-cysteine, bFGF, folic acid, cholic acid and CXCL12.

0.57 mM of L-cysteine,
   40 ng/mL of bFGF,
   1.6 μL/mL of L-alanyl-L-glutamine dipeptide,
   50 μM of folic acid,
   2 μg/mL of cholic acid, and
   50 ng/mL of CXCL12.

3. A culture method for in vitro maturation of bovine oocytes using the serum-free culture medium of claim 1, comprising:

pre-heating the serum-free culture medium; and
culturing the bovine oocytes in the pre-heated serum-free culture medium at 38.5° C. and 5% $CO_2$ under saturated humidity for 18-22 h to obtain mature bovine oocytes;
wherein the serum-free culture medium comprises a Hepes-free M199 basal medium,
2-8 mg/mL of fatty acid-free BSA,
0.05-0.1 IU/mL of human menopausal gonadotrophin (HMG),
0.1-2 μg/mL of 17 β-estradiol,
1-100 ng/mL of epidermal growth factor (EGF),
0.1-1 mM of L-cysteine,
1-100 ng/mL of bFGF,
0.5-2 μL/mL of L-alanyl-L-glutamine dipeptide,
1-100 μM of folic acid,
1-10 μg/mL of cholic acid and
1-100 ng/mL of CXCL12.

4. The culture method of claim 3, wherein the bovine oocytes are germinal vesicle (GV) stage.

5. The culture method of claim 4, wherein the pre-heating is performed for 1-3 h.

6. The culture method of claim 5, wherein the pre-heating is performed at 38.5° C. and 5% $CO_2$ under saturated humidity.

7. The culture method of claim 6, wherein an initial density in the culturing is 40-50 bovine oocytes per 500 μL of the serum-free culture medium.

\* \* \* \* \*